United States Patent [19]

Rosenthal et al.

[11] Patent Number: 5,284,777
[45] Date of Patent: Feb. 8, 1994

[54] COMBINED GLYCATED HEMOGLOBIN AND IMMUNOTURBIDOMETRIC GLYCATED ALBUMIN ASSAY FROM WHOLE BLOOD LYSATE

[75] Inventors: Murray A. Rosenthal, Copley; David R. Hocking, Akron, both of Ohio

[73] Assignee: Isolab, Inc., Akron, Ohio

[21] Appl. No.: 664,401

[22] Filed: Mar. 4, 1991

[51] Int. Cl.$^5$ .................. G01N 33/53; G01N 33/536; G01N 33/68
[52] U.S. Cl. .................... 436/518; 436/87; 436/88; 436/67; 436/17; 436/536; 436/825
[58] Field of Search ............... 436/518, 815, 548, 824, 436/825, 808, 536, 87, 88, 67, 17; 530/387

[56] References Cited

U.S. PATENT DOCUMENTS

| | | | |
|---|---|---|---|
| 4,269,605 | 5/1981 | Dean | 23/230 |
| 4,594,327 | 6/1986 | Zuk | 436/514 |
| 4,778,752 | 10/1988 | Curtiss et al. | 530/387 |
| 4,797,473 | 1/1989 | Tarsio et al. | 530/387 |
| 4,806,468 | 2/1989 | Wagner et al. | 435/188 |

FOREIGN PATENT DOCUMENTS

| | | | |
|---|---|---|---|
| 8800346 | 1/1988 | European Pat. Off. | 435/7.92 |
| 8906798 | 7/1989 | European Pat. Off. | 435/7.9 |

OTHER PUBLICATIONS

*Fundamentals of Clinical Chemistry*, Ed. by N. Tietz, W. B. Saunders Company, Philadelphia, pp. 108–114, 1976.
Complete Disposable System for Quantitating Glycohomoglobins 1986 Isolab, Inc.
Accessory Kit for Use with Glyc-Affin GHb to Measure Glycated Albumin in Human Serum or Plasma, Isolab, Inc. Feb. 15, 1991.
Precise Measurement of Glycated Serum Albumin by Column Affinity Chromatography and Immunoturbidity, Reed, Paul et al (1986).

*Primary Examiner*—Esther L. Kepplinger
*Assistant Examiner*—Toni R. Scheiner
*Attorney, Agent, or Firm*—Roger A. Gilcrest

[57] ABSTRACT

A method and kit for the isolation and quantitation of glycated hemoglobin and other glycated proteins, specifically albumin, from a single sample of whole blood. Glycated hemoglobin is calculated from an eluate resulting from the contact of the whole blood hemolysate with a boronated resin. Glycated albumin and other plasma proteins are calculated using immunoturbidimetry, resulting from reaction between a buffered antibody solution and the albumin or other protein in the previous eluate.

11 Claims, No Drawings

COMBINED GLYCATED HEMOGLOBIN AND IMMUNOTURBIDOMETRIC GLYCATED ALBUMIN ASSAY FROM WHOLE BLOOD LYSATE

TECHNICAL FIELD

The present invention relates, generally, to the measurement of glycated proteins and more specifically to the isolation and quantitation of glycated albumin from a sample of whole blood, as a measure of diabetic control and the combining of this method with the quantitation of glycated hemoglobin from the same sample into a single assay.

BACKGROUND OF THE INVENTION

Glycated proteins, specifically glycated albumin and glycated hemoglobin, are useful indicators of diabetic control. Hemoglobin, albumin and other plasma proteins are continuously glycated in the blood stream, nonenzymatically, by the reaction of glucose with the terminal free amino group of the protein, slowly forming a Schiff base which subsequently undergoes an Amadori rearrangement to form an essentially stable ketoamine.

The degree of glycation of these proteins is directly proportional to the circulating glucose concentration. Thus, measurement of the degree of glycation, specific or nonspecific, provides an accurate reflection of blood glucose levels over the life-span of that protein.

Due to the life-span of hemoglobin, levels of glycated hemoglobin represent an indicator of average blood glucose levels, and therefore diabetic control, over a period of the previous one to two months. Albumin and other plasma proteins have a much shorter serum half-life (approximately 14 days for serum albumin) than hemoglobin. However, because of this fact these proteins serve as useful indicators of average blood glucose levels over the previous 1-3 weeks. Such indicators are of value in unstable diabetics who require careful monitoring or in the evaluation of revised drug, diet or insulin regimens.

A currently accepted methodology for the isolation of glycated hemoglobin, albumin and other proteins is affinity chromatography performed using boronated agarose columns. Assays for both glycated hemoglobin and glycated proteins are disclosed in U.S. Pat. No. 4,269,605 to Dean.

Utilizing currently known techniques, in order to measure for both glycated hemoglobin and glycated albumin in a sample, two separate columns must be run. A whole blood hemolysate is used in the assay of glycated hemoglobin and a serum or plasma sample used to assay glycated albumin. A number of kits are commercially available for separating the glycated hemoglobin from the non-glycated hemoglobin. One such kit is made by Isolab, Inc. and sold under the trademark Glyc-Affin ® GHb. An accessory kit sold under the trademark Glyc-Affin ® PGA is used with the former to measure glycated albumin in serum or plasma.

As previously stated, in order to measure glycated hemoglobin a sample of whole blood hemolysate is used. This hemolysate contains both hemoglobin and plasma proteins, including albumin. However, up to now, colormetric interference from the hemoglobin in the sample was thought to prevent accurate colormetric evaluation of glycated albumin from the same eluate. Additionally, the resulting eluate contained an amount of albumin below the capable detection range of the measuring assays. Turbidimetry refers to the measurement of transmitted light intensity at a 0° angle. Immunoturbidimetry is essentially the same process whereby the turbidity in solution is created by an antigen/antibody complex. This process has been used in the calculation of glycated albumin content from serum or plasma (Reed P, Bhatnagar D, Dhar H., Winocour P. (1986) Precise Measurement of Glycated Serum Albumin by Column Affinity Chromatography and Immunoturbidimetry. Clinica chimica Acta 161:191-199). In an analysis for glycated albumin, albumin is the antigen to which the an anti-albumin antibody complexes. This insoluble complex produces a measurable turbidity in the solution proportional to the amount of antigen present and is measured by absorbance. However, as previously stated, this same process was not performed on an eluate of a whole blood sample due to the colormetric interference with hemoglobin. Additionally, it had not been shown that albumin could be separated into its glycated and nonglycated forms in a whole blood sample using current methodology.

Due to the deficiencies in the prior art and, specifically, the inability of known testing methods to isolate and quantitate glycated hemoglobin and glycated albumin from a single affinity chromatography column, the subsequent invention is herein presented.

DISCLOSURE OF THE INVENTION

This invention presents a method for isolating and quantitating both glycated hemoglobin and glycated albumin from a whole blood sample utilizing a single affinity chromatography column. We have determined that proteins, such as albumin as well as hemoglobin, are separated into glycated and nonglycated fractions during chromatography of a hemolyzed whole blood sample.

It is therefore an object of the present invention to present a method for quantitating glycated albumin from a whole blood sample and a kit for said purpose.

It is a further object of the present invention to combine the isolation and measurement of glycated albumin and glycated hemoglobin into a single assay or kit.

It is a still further object of the present invention to provide a single reliable kit for the evaluation of short-term (1-3 weeks) and intermediate (1-2 months) blood glucose levels in patients with diabetes, calculated from a single whole blood sample on a single chromatography column run.

It is yet a further object of the present invention to provide an assay method for measuring glycated albumin from a sample of whole blood without interference from hemoglobin present in the sample.

It is a still further object of this present invention to provide's single assay for the measurement of glycated hemoglobin (GHb) and glycated albumin (GA) which saves the utilizing clinician both the time and expense of running more than 1 column for a single blood sample.

BEST MODE FOR CARRYING OUT THE INVENTION

In one aspect of the present invention, a sample of whole blood is collected and treated to form a hemolysate. It is preferred that a freshly drawn fasting blood sample be used when possible as high levels of glucose in the sample may cause interference with the binding of glycated protein to the affinity matrix.

The hemolysate is introduced into a boronated affinity column utilizing phenylboronic acid coupled to agarose or other polysaccharide matrix. Such columns as well as the method of isolating glycated proteins from serum and glycated hemoglobin from whole blood are disclosed in U.S. Pat. No. 4,269,605 to Dean and available in such commercial kits as Isolab's Glyc-Affin ® Kit and as such both references are and incorporated by reference.

In summary, the modified steps involved in the present method are as follows:

1. Using a sample of whole blood hemolysate, glycated proteins, including hemoglobin and albumin in the hemolysate to bind the boronic component of the column;

2. Non-glycated proteins are removed by washing the column and the resulting eluate set aside;

3. The glycated proteins are removed from the column and collected using a reagent containing a desorption component, preferably not removing the boronic component from the column.

4. Assay the collected eluates for the hemoglobin component, by known methods such as spectrophotometry at a wavelength of 415 nm.

It is from these same collected eluates, from which the glycated hemoglobin has been determined, that glycated albumin is quantitated as explained subsequently and as illustrated in the following examples.

Although the eluates from which glycated albumin can now be quantitated as#is disclosed as having been obtained through affinity chromatography using a boronated agarose column, it is to be recognized that such eluates could be obtained using a number of other separation formats, reagent compositions or detection methods as are well known in the art. Column separation can be performed manually or by automated instrumentation and eluding forces other than gravitational force are contemplated. Separation is also contemplated using batching techniques wherein the sample is mixed with a boronated solid phase and the resulting complex is isolated by physical means such as filtration, decanting, centrifuging, magnetism or other means known in the art.

Quantitation of the glycated albumin fraction from the eluate is determined using immunoturbidimetry. A goat polyclonal antihuman albumin antibody is diluted in a phosphate buffered saline solution and a predetermined amount of the resulting antibody solution is added to the eluate. The antibody is disclosed as a polyclonal goat antihuman albumin obtained commercially from Atlantic Antibodies, Scarborough, Maine but the antibody used in this immunoturbidimetric assay is contemplated as monoclonal or polyclonal and may be isolated from any species of animal provided it reacts with the human albumin to form a turbid solution.

The preferred antibody reagent is prepared by mixing the selected antibody with a saline solution buffered to a pH of preferably about 7.4. One such solution used contains:
900 mL water
9.0 g sodium chloride
1.15 g sodium phosphate dibasic
0.2 g potassium phosphate monobasic
50 g polyethylene glycol 8000 (PEG)
0.5 g sodium azide to pH 7.4 with 8N sodium hydroxide quantity sufficient (QS) to 1000 ml with water.

The kit for isolating and measuring the amount of glycated hemoglobin and glycated albumin from whole blood samples contains a plurality of boronated agarose affinity columns, a column preparation solution, a first fraction elution agent to remove the nonglycated proteins from the column, a second fraction elution agent to desorb the glycated proteins from the column for collection, a buffered saline solution for preparation of the antibody reagent, a selected antibody which will react with albumin or other protein to form a turbid solution.

The invention is illustrated in and by the following examples:

EXAMPLE I

Glyc-affin ® GHb and Glyc-affin ® GA kits (Isolab, Inc.) were used to determine glycated hemoglobin and glycated albumin values, respectively, on four samples. On these samples, glycated hemoglobin was determined using a sample of whole blood and glycated albumin was determined using a serum, both obtained from the same subjects. This assay was conducted using an affinity column for the whole blood hemolysate and a second affinity column for the serum with respect to each subject. These values are reported in Table I as "current assays".

TABLE I

| COMPARISON STUDY CURRENT VS. COMBINED ASSAY | | | |
|---|---|---|---|
| SAMPLE I.D. | CURRENT % GHb | CURRENT % GA | COMBINED % GA |
| A4 diabetic | 10.3% | 11.3% | 10.2% |
| A6 diabetic | 10.4% | 12.6% | 11.5% |
| E1 normal | 6.4% | 9.0% | 7.5% |
| E2 normal | 5.7% | 8.9% | 7.6% |

The residual eluates from the glycated hemoglobin assay were then loaded onto a COBAS BIO centrifugal analyzer (Roche, Nutley, NJ) with the DENS option. An antibody reagent solution was prepared by taking 25 mL of the phosphate buffered saline solution and adding 1 ML of goat antihuman albumin. The resulting solution was mixed, allowed to stand for approximately 30 minutes and filtered through a 0.2 micron membrane.

The centrifugal analyzer mixed each sample with the antibody reagent solution in the amounts illustrated in Table II and thereafter, took absorbance readings at 0.5 and 300 seconds at a wavelength of 340 nm.

A standard curve was calculated from dilutions of human albumin (Sigma, St. Louis, Missouri) in isotonic saline. The instrument calculated the concentration of albumin in each eluate using a curve fitting model. From these concentrations, the percentage of glycated albumin is calculated using the following mathematical formula which takes into account the dilution of the nonglycated column eluate.

$$\% \text{ Glycated Fraction (albumin)} = \frac{100x}{10Y + x}$$

Where X=absorbance of the glycated fraction and Y=absorbance of nonglycated fraction.

The parameters under which the samples were analyzed are found in Table II below:

TABLE II

| TEST NR 25 + ALBUMIN | COBAS BIO |
|---|---|
| 1 UNITS | MG/DL |
| 2 CALCULATION FACTOR | .1000 |
| 3 STANDARD 1 CONC | .2439 |

TABLE II-continued

| TEST NR 25 + ALBUMIN | COBAS BIO |
|---|---|
| 3 STANDARD 2 CONC | .4878 |
| 3 STANDARD 3 CONC | .9755 |
| 3 STANDARD 4 CONC | 1.951 |
| 3 STANDARD 5 CONC | 2.927 |
| 3 STANDARD 6 CONC | 3.902 |
| 6 LIMIT | 0 |
| 7 TEMPERATURE [DEG. C.] | 25.0 |
| 8 TYPE OF ANALYSIS | 7.5 |
| 9 WAVELENGTH [NM] | 340 |
| 10 SAMPLE VOLUME [UL] | 07 |
| 11 DILUENT VOLUME [UL] | 20 |
| 12 REAGENT VOLUME [UL] | 200 |
| 13 INCUBATION TIME [SEC] | 0 |
| 14 START REAGENT VOLUME [UL] | 0 |
| 15 TIME OF FIRST READING [SEC] | .5 |
| 16 TIME INTERVAL [SEC] | 300 |
| 17 NUMBER OF READINGS | 02 |
| 18 BLANKING MODE | 1 |
| 19 PRINTOUT MODE | 1 |

In a comparison of the glycated albumin assay performed on the eluate isolated from the whole blood sample compared to the known assay from a serum sample, it can be seen that the results are reasonably matched. The absorbance of glycated albumin from the whole blood sample is run at a wavelength ranging from about 340 nm to about 380 nu in order to avoid interference with the absorbance of hemoglobin in the sample. Glycated albumin can be calculated from the absorbance response of the albumin/antibody complex.

EXAMPLE 2

Whole blood and serum samples from two subjects were run as in Example I with the following changes:
1. The antibody diluent contained 7.5% PEG.
2. Antibody (1 mi) was mixed with 40 mL antibody diluent.
3. COBAS BIO program parameters are found in Table 3 below:

TABLE III

| TEST NR 25 + ALBUMIN | COBAS BIO |
|---|---|
| 1 UNITS | MG/DL |
| 2 CALCULATION FACTOR | .1000 |
| 3 STANDARD 1 CONC | .2439 |
| 3 STANDARD 2 CONC | .4878 |
| 3 STANDARD 3 CONC | .9755 |
| 3 STANDARD 4 CONC | 1.951 |
| 3 STANDARD 5 CONC | 2.927 |
| 3 STANDARD 6 CONC | 3.902 |
| 6 LIMIT | 0 |
| 7 TEMPERATURE [DEG. C.] | 25.0 |
| 8 TYPE OF ANALYSIS | 7.1 |
| 9 WAVELENGTH [NM] | 380 |
| 10 SAMPLE VOLUME [UL] | 75 |
| 11 DILUENT VOLUME [UL] | 10 |
| 12 REAGENT VOLUME [UL] | 75 |
| 13 INCUBATION TIME [SEC] | 0 |
| 14 START REAGENT VOLUME [UL] | 0 |
| 15 TIME OF FIRST READING [SEC] | .5 |
| 16 TIME INTERVAL [SEC] | 300 |
| 17 NUMBER OF READINGS | 02 |
| 18 BLANKING MODE | 1 |

TABLE III-continued

| TEST NR 25 + ALBUMIN | COBAS BIO |
|---|---|
| 19 PRINTOUT MODE | 1 |

Program changes from that in Table II were made in type of analysis, wavelength, sample volume, diluent volume and reagent volume. The program changes alter the read times used in the calculations. Additionally a blank reading (auxiliary reading) is taken on the sample prior to the addition of the antibody.

4. The glycated hemoglobin columns in this example were run on the Hamilton Microlab 2200 (Hamilton, Reno, Nevada), an automated liquid transfer instrument adapted to run columns. The Microlab 2200 pipettes the eluates into a 96-well microtiter plate for analysis on a Biotek EL312 plate reader (Winooski, Vermont). The hemoglobin absorbance was read directly at 415 nm. For glycated albumin, 100 uL of antibody solution above was added to 100 uL of eluate already in the plate. The blank reading on the plate was taken prior to the addition of antibody. A second reading was taken 10 minutes after addition of the antibody. Both readings were performed at 380 nm. Results were calculated from the raw absorbance data, and not from calculated curves.

5. Coefficient of variation values (CV) are also listed for the combined glycated albumin methods in Table IV:

TABLE IV

| | COMPARISON STUDY CURRENT VS. COMBINED ASSAY | | | | | |
|---|---|---|---|---|---|---|
| | MICROLAB | | COBAS BIO COMBINED | | MICROLAB COMBINED | |
| | CURRENT | CURRENT | | | | |
| SAMPLE I.D. | % GHb | % GA | % GA | % CV | % GA | % CV |
| KT normal | 5.8 | 7.6 | 7.4 | 2.0 | 7.6 | 2.9 |
| MU diabetic | 13.3 | 11.7 | 10.9 | 3.5 | 10.1 | 3.0 |

These results show the glycated albumin values generated from the combined glycated hemoglobin/glycated albumin assays produced values similar to the results generated by current assays. These results further show the effectiveness of an alterative blanking procedure. This assay can be automated so that several (up to 96 on the Microlab 2200) columns can be run at the same time. Precision of the Cobas BIO and Biotek Readers are similar. The absorbance response for these instruments was also similar; cobas BIO 0.078, and Biotek 0.076 (final absorbance minus blank absorbance for the glycated fraction of sample MU). The results further show that glycated albumin values calculated on a standard curve are equivalent to those obtained using blank corrected absorbance readings.

EXAMPLE 3

Whole blood and serum samples from 12 subjects were run as in Example 2 on the Microlab 2200 except that the antibody dilution was 1 mL in 75 mL of diluent. Values were calculated directly from absorbance data with readings taken at both 5 and 25 minutes.

TABLE V

| | COMPARISON STUDY CURRENT VS. COMBINED ASSAY | | | |
|---|---|---|---|---|
| | CUR-RENT | CUR-RENT | 5 MIN. COMBINED | 25 MIN. COMBINED |
| SAMPLE I.D. | % GHb | % GA | % GA | % GA |
| A3 | 15.8 | 16.1 | 14.6 | 14.8 |
| A4 | 5.7 | 7.4 | 7.1 | 6.6 |

TABLE V-continued

COMPARISON STUDY CURRENT VS. COMBINED ASSAY

| SAMPLE I.D. | CURRENT % GHb | CURRENT % GA | 5 MIN. COMBINED % GA | 25 MIN. COMBINED % GA |
|---|---|---|---|---|
| A7  | 9.9  | 11.3 | 10.5 | 10.9 |
| B6  | 6.8  | 9.3  | 8.9  | 8.3  |
| B10 | 6.1  | 7.7  | 6.8  | 6.5  |
| B20 | 12.4 | 12.2 | 11.3 | 10.4 |
| C4  | 5.6  | 7.0  | 6.3  | 6.6  |
| C6  | 4.6  | 6.4  | 6.1  | 6.2  |
| C8  | 5.4  | 6.7  | 6.7  | 6.9  |
| D1  | 10.7 | 12.2 | 10.7 | 10.9 |
| D3  | 10.9 | 13.0 | 11.3 | 11.5 |
| D7  | 7.5  | 9.7  | 8.8  | 8.5  |

The results in this example illustrate that an increased reaction time has no significant effect. Also, results calculated using raw absorbance data are similar to those obtained from the standard curve used in the current assays. Therefore, it is shown that the values of glycated albumin obtained from a combined glycated albumin/glycated hemoglobin assay are similar to those obtained from separated assays of glycated hemoglobin using whole blood sample and glycated albumin using serum or plasma.

EXAMPLE 4

This example was run on the Hamilton Microlab 2200 as in Example 2. Plasma was recovered from packed red cells after centrifugation. Increasing proportions of the packed cells were mixed with the plasma.
Results:

TABLE VI

HEMOGLOBIN INTERFERENCE

| % PACKED CELLS | % GA |
|---|---|
| 20 | 11.7 |
| 30 | 11.9 |
| 40 | 11.5 |
| 50 | 11.2 |
| 60 | 11.5 |
| 70 | 11.5 |

As expected, samples produced substantially identical glycated albumin levels at varying concentrations of hemoglobin. Thus, the results illustrate that the presence of hemoglobin does not interfere with the combined glycated hemoglobin/glycated albumin assay.

EXAMPLE 5

Five samples were run on columns as in Example 1. the eluate absorbance for Hb was read as in Example 2. The eluate albumin concentration was read as in Example 2 using the plate reader technique. After manual addition of 150 uL of each eluate, the sample blank (SB) on the plate was read. This was followed by 150 uL addition of the antibody reagent. To calculate %GA, an alternate blanking method was used. We subtracted a reagent blank (RB), which was the absorbance reading of a well with 150 uL of water and 150 uL of antibody reagent, and one-half of the SB from each eluate absorbance. From this, we calculated the results using the formula in Example 1. Absorbance responses and the calculation for sample A25 were:

TABLE VII

ABSORBANCE RESPONSES AND CALCULATION SAMPLE A25

| Reading | Nonglycated (NG) Eluate | Glycated (G) Eluate |
|---|---|---|
| RB | .0435 | .0435 |
| SB | .0350 | .0500 |
| + Antibody (AB) | .1230 | .1770 |

Calculation:

$$G \text{ or } NG = Ab - (0.5 \times SB) - RB$$
$$NG = .1230 - (0.5 \times .0350) - .0435 = .0620$$
$$G = .1770 - (0.5 \times .0500) - .0435 = .1085$$
$$\% GA = (100\% \; G)/((10 \times NG) + G)$$
$$= (100\% \times .1085)/(10 \times .0620) + .1085) = 14.9\%$$

Results of this study are presented here:

TABLE VIII

COMPARISON STUDY CURRENT VS. COMBINED ASSAY

| SAMPLE I.D. | CURRENT % GHb | CURRENT % GA | COMBINED % GA |
|---|---|---|---|
| A25 | 11.7 | 14.8 | 14.9 |
| B7  | 8.8  | 11.2 | 11.5 |
| C15 | 5.4  | 7.6  | 7.4  |
| D12 | 8.4  | 8.7  | 8.5  |
| E8  | 12.4 | 16.6 | 16.7 |

This shows that this blanking procedure results in values almost identical to the current Clyc-Affin GA assay.

EXAMPLE 6

A sample consisting of washed hemolyzed red cells was run as in Example 5. The washing was done to remove protein and albumin from the sample. The current %GHb was 5.8%. The following absorbencies (380 nm) were obtained from the albumin assay:

TABLE IX

ABSORBANCE RESPONSES OF WASHED SAMPLE

| Reading | Nonglycated (NG) Eluate | Glycated (G) Eluate |
|---|---|---|
| RB | .0435 | .0435 |
| SB | .0270 | .0200 |
| + Antibody (AB) | .0570 | .0580 |
| | NG = .0000 | |
| | G = .0045 | |

Thus a non-albumin containing hemoglobin sample gave a minimal response in the albumin assay. This is further proof that hemoglobin does not interfere with the GA assay.

While the foregoing examples illustrate the quantitation of glycated albumin from a sample of whole blood, substantially similar assays can be performed for the quantitation of other specific plasma proteins, such as transferrin or total plasma protein. Antibodies demonstrating specificity toward the desired protein (antigen) can be selected by those of ordinary skill in the art or in the assay of total proteins less specific antibodies, such as those against whole human serum are also known.

While in accordance with the patent statutes, the best mode and preferred embodiment of the invention have been described, it is to be understood that the invention is not limited thereto, but rather is to be measured by the scope and spirit of the appended claims.

We claim:

1. A method of quantitating a glycated non-hemoglobin protein in a whole blood lysate, said method comprising the steps of:
   (a) separating glycated proteins from non-glycated proteins by contacting said lysate with a boronated affinity column, to obtain an eluate containing glycated hemoglobin and at least one glycated non-hemoglobin protein;
   (b) contacting said eluate with an antibody which specifically binds said non-hemoglobin protein, said antibody being in solution buffered to a Ph of from about 7.0 to 9.0, whereby turbidity is produced in said solution; and
   (c) determining the amount of said non-hemoglobin protein in said turbid solution by measuring said turbidity.

2. The method according to claim 1 wherein said glycated non-hemoglobin protein comprises albumin.

3. The method according to claim 3 wherein said turbidity is determined by measuring the amount of light transmitted through said solution.

4. The method according to claim 3 wherein said transmitted light is measured at a wavelength of about 305 to about 405 nanometers.

5. The method according to claim 4 wherein said transmitted light is measured at a wavelength of about 340 to about 380 nanometers.

6. The method according to claim 1 wherein said antibody is a polyclonal antibody.

7. The method according to claim 1 wherein said antibody is a goat antihuman antibody.

8. The method according to claim 1 wherein said antibody specifically binds albumin in said solution.

9. A method of determining amounts of glycated non-hemoglobin protein present in a sample of whole blood containing glycated hemoglobin, said method comprising the steps of:
   (a) lysing said sample of whole blood;
   (b) contacting said lysed sample of whole blood with a boronated resin to absorb glycated proteins, said glycated proteins comprising glycated hemoglobin and at least one glycated non-hemoglobin protein;
   (c) eluting an eluate containing said glycated proteins from said boronated resin;
   (d) contacting said eluate with an antibody which specifically binds said at least one non-hemoglobin glycated protein, said antibody being in a solution buffered to a pH of from about 7.0 to 9.0, whereby turbidity is produced in said solution; and
   (e) determining the amount of said at least one glycated non-hemoglobin protein in said solution by measuring said turbidity and comparing said turbidity to that of a standard to quantitate the amount of said at least one glycated non-hemoglobin protein.

10. The method according to claim 9 further comprising the step of determining the amount of glycated hemoglobin in said eluate, said step occurring after step (c).

11. The method according to claim 9 wherein said at least one non-hemoglobin glycated protein is albumin.

* * * * *